United States Patent [19]

Eldridge, Jr.

[11] 4,336,806
[45] Jun. 29, 1982

[54] MEDICAL TUBING HOLDER

[75] Inventor: John Eldridge, Jr., Balboa Island, Calif.

[73] Assignee: Instranetics, Inc., Tustin, Calif.

[21] Appl. No.: 147,632

[22] Filed: May 7, 1980

[51] Int. Cl.³ .................. A61M 25/00; F16L 3/08
[52] U.S. Cl. .................... 128/348; 128/DIG. 26; 128/133; 248/205 A; 248/75; 248/74 PB; 335/285; 335/303; 24/201 B
[58] Field of Search .......... 128/DIG. 26, 133, 214 R, 128/214.4, 215, 221, 165, 348, DIG. 6; 248/205 A, 75, 74 PB, 467; 269/8; 335/303, 285; 24/201 B

[56] References Cited

U.S. PATENT DOCUMENTS

| 361,248 | 4/1887 | Winton | 335/285 |
|---|---|---|---|
| 2,597,601 | 5/1952 | Sherman | 335/303 X |
| 3,063,118 | 11/1962 | Salter et al. | 335/285 X |
| 3,421,187 | 1/1969 | Ryder | 248/74 PBX |
| 3,430,300 | 3/1969 | Doan | 128/DIG. 26 X |
| 3,727,658 | 4/1973 | Eldridge, Jr. | 150/52 R |
| 3,826,254 | 7/1974 | Mellor | 128/DIG. 26 X |
| 3,944,069 | 3/1976 | Eldridge, Jr. | 206/350 |
| 4,165,748 | 8/1979 | Johnson | 128/DIG. 26 X |
| 4,258,493 | 3/1981 | Kettlestrings et al. | 24/201 B |

FOREIGN PATENT DOCUMENTS 778279  2/1968  Canada ................ 335/303

OTHER PUBLICATIONS

Pharmaseal K99, Tube and Cord Holder Device, Pharmaseal Lab., Glendale, Cal. 91201

Primary Examiner—Gene Mancene
Assistant Examiner—Mickey Yu
Attorney, Agent, or Firm—Knobbe, Martens

[57] ABSTRACT

A medical tube holder and its method of use are disclosed. The holder has a backing strip having front and back faces, a portion of the back face being adapted to adhere to a substrate, such as a surgical drape. The backing strip has preferential tube receiving locations and is movable between a folded and unfolded position. Members possessing a mutual magnetic attraction are mounted on the front surface of the strip for mutual engagement when the strip is folded. The tubing is secured within the preferential receiving locations between folded sections of the strip when the strip is in its folded position.

3 Claims, 10 Drawing Figures

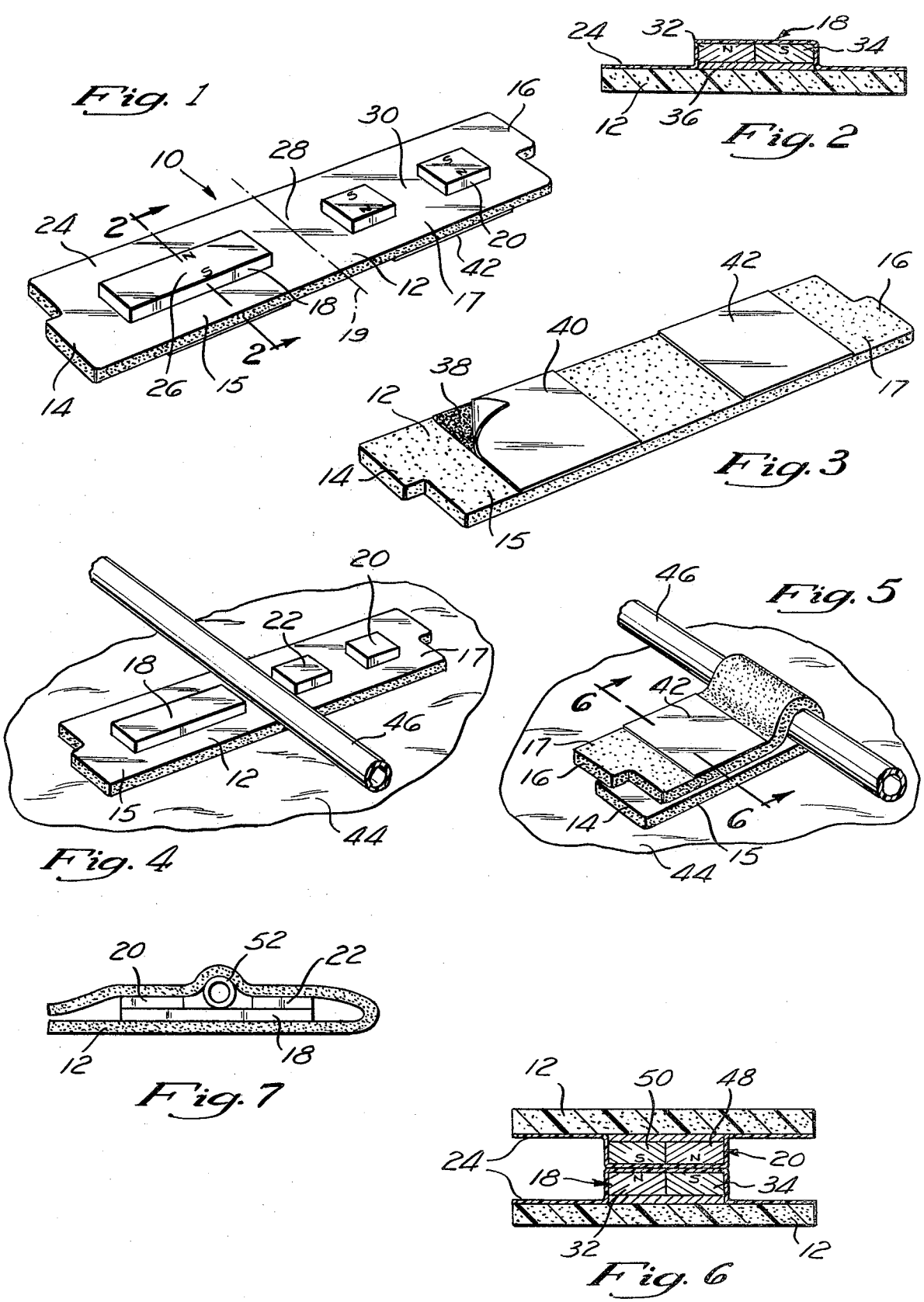

U.S. Patent  Jun. 29, 1982  Sheet 2 of 2  4,336,806
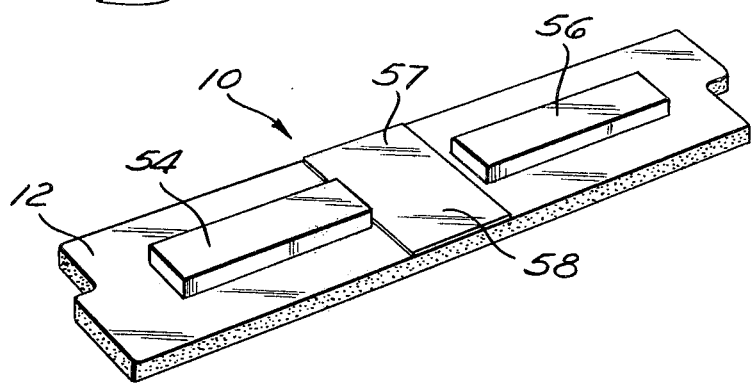
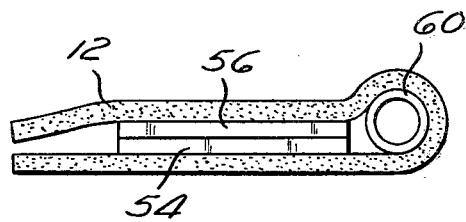
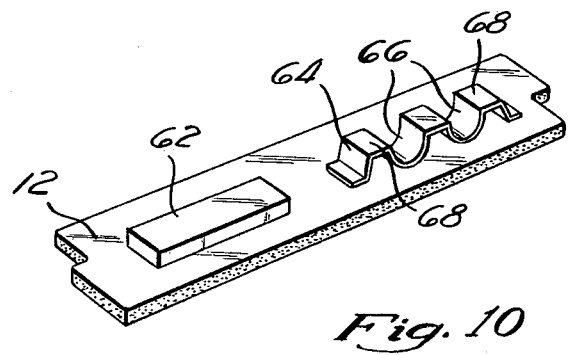

MEDICAL TUBING HOLDER

BACKGROUND OF THE INVENTION

The invention generally relates to holders for medical tubing, such as vacuum tubes, electrical cords, and the like, which are often employed in surgical operations.

Throughout a hospital, tubing and cords of various types are used in health care operations and particularly during surgery. Often there is a need to be able to temporarily anchor such tubing. After being deposited, the tubing must be easily retrievable for further use during the particular operation and, in addition, there is a need to improve the ability of the physician or nurse involved in the operation to control and handle such tubing. Thus, it is often advantageous that the tubing be easily slidable while deposited to permit the required manipulation of the tubing. It is also advantageous to be able to control the amount of holding power of the anchoring device.

For example, vacuum tubes, which are used to remove accumulating blood or other fluids during surgery, must be readily accessible throughout the operation and yet not be an obstruction. Nasal gastric tubes are inserted into the patient's nostril and are used to siphon fluids from the patient's stomach. There is a need to be able to anchor and adequately control the nasal gastric tubing which extends from the patient's nostrils. If a cautery is employed during an operation, there is a need to be able to anchor and manipulate the cautery cord which extends from the instrument. A further example of tubes which require manipulation or anchoring are the tubes which extend from intravenous bottles that are used to provide nourishment to the patient.

Typically, a patient, during an operation is covered with a surgical towel or drape which is made of paper or cloth. Such a drape serves as a convenient location to attach a tubing holder since the holder so deposited is in close proximity to the focus of the operation without being an obstruction to the physician or nurse. However, it is important that when the tubing is removed from the holder, the holder not tear the drape. If the drape is torn, bacteria from the wound might contact the sterile instruments being used in the operation. It is also advantageous that when the tubing is removed from the holder, the holder remain affixed to the drape so as to not obstruct the operation in any way. Prior tubing holders have been unable to satisfy the need for a holder which easily anchors such tubing and permits its prompt release if the tubing is pulled without tearing the drape or disengaging from the drape.

Tubing, such as nasal gastric tubes, inserted into a patient's nostrils, are often held in place by surgical tape affixed to the bridge of the patient's nose or other facial location. This method of holding is unsatisfactory since movement of the tubing, such as caused by the patient's motions, can cause the tubing to irritate the patient's nostrils. There is, therefore, a requirement for the tubing to be released from its holder if the tubing is pulled, such as by sudden movement of the patient.

One known prior device has a square support pad with front and back faces. An adhesive is applied to the back surface so that the pad can be affixed to a substrate, such as a surgical drape. The front or upper surface of the pad is made of felt. One portion of the support pad is a rectangular strip which can be wound around a tube. The end of the strip or pad has a Velcro ® pad which is attached to the felt surface, thereby holding the tube in place. The tube may be affixed to permit slide or no slide, depending upon whether the pad is wound around the tube so as to contact the tube with the adhesive side of the strip.

This device has been found unsatisfactory since the Velcro ® has a tendency to snag the gloves used by the nurses and surgeons. In addition, the device requires complicated winding procedures in order to affix it to the holder. Thirdly, if the tubing is pulled before it is released, the device has a tendency to tear the surgical drape upon which the pad is affixed. Finally, this device does not allow the operator to control the amount of holding power applied to the tubing.

There is, therefore, a need for an effective device which will hold medical tubing and yet provide for easy manipulation and quick release of such tubing without damage to or detachment from the surface upon which the holder is affixed.

SUMMARY OF THE INVENTION

The disclosed invention obviates the difficulties involved in prior tubing holder devices. The device has a backing strip with front and back faces, a portion of the back face being adapted to adhere to a substrate, such as a surgical drape. The strip is flexible so as to be movable between folded and unfolded positions, and has preferential tube receiving locations. Members having a mutual magnetic attraction are mounted on the front surface of the strip for mutual engagement when the strip is folded. At least one member is a magnet with the other members being magnetizable materials. The size and number of the magnets and/or magnetizable elements may be varied. In a preferred embodiment, the members are spaced to provide the locations to receive the medical tubing. Thus, when the strip is folded, the tubing is secured between folded sections of the strip. In this way, the degree in which the tubing is held by the device can be controlled by varying the strength of the magnetic attraction between the members. The tubing is easily released from the holder by simply pulling up on the tubing or finger tabs provided, thereby disengaging the members from one another and unfolding the backing strip.

A section of the back surface of the strip has an adhesive so that the device can be affixed to a substrate, such as a surgical drape. The magnetic attraction of the members to each other is less than the adhesion of the strip to the surgical drape to permit the unfolding of the strip without damage to the drape or disengagement of the strip from the drape.

In one embodiment, employing multiple magnets, the magnets include a pair of contiguous magnet portions of opposite polarity to ensure maximum contact of the upper surfaces of the magnets when the strip is in its folded position. This ensures that the folded sections of the strip are properly aligned in the folded configuration, thereby increasing the holding power of the device.

In a further embodiment, an adhesive may be applied to the front surface of the strip in contact with the tubing. The adhesive may be covered with a peel-away material of a substantially lower coefficient of friction than the strip, such as silicone. Thus, if the silicon covering is left in place, the tubing is exceedingly easy to slide between the folded portions of the strip. Conversely, if the silicone covering is peeled away, thereby exposing the adhesive, the tubing is not slidable.

The backing strip may also be applied to the skin of the patient to improve the handling of surgical tubing, such as nasal gastric tubes which are inserted into the patient. For example, the backing strip can be applied to the forehead of the individual to hold the tubing which is inserted in the patient's nostrils. The tubing is easily releasable if pulled so that the patient's nostrils will not be damaged if the tubing is stretched, such as from movements by the patient.

The invention holder is also useful in anchoring and improving the manipulation of cautery cords and tubes which extend from intravenous bottles. In the latter situation, the holder may be applied to the rod which supports the intravenous bottle.

DESCRIPTION OF THE DRAWINGS

These and other advantages will be clarified by the discussion below and reference to the drawings in which:

FIG. 1 is a perspective view of a preferred embodiment of the inventive device, showing the backing strip and magnets mounted thereon;

FIG. 2 is a cross-sectional view taken along line 2—2 of the backing strip and magnet as shown in FIG. 1;

FIG. 3 is a perspective view of the back surface of the backing strip of FIG. 1 showing two peel-away adhesive portions;

FIG. 4 is a perspective view of the device of FIG. 1 shown affixed to a surgical drape by means of one of the adhesives portions of FIG. 2 and showing a portion of tubing positioned between two magnets;

FIG. 5 is a perspective view showing the backing strip of FIG. 4 in its folded position;

FIG. 6 is a cross-sectional view taken along lines 6—6 showing the magnets with their respective polarities in mutual engagement;

FIG. 7 is a side view of the backing strip in its folded position with tubing positioned between the two smaller magnets shown in FIG. 1;

FIG. 8 is a perspective view of an alternate embodiment of the invention in which two bar magnets are shown mounted to the backing strip and a peel-away portion positioned between the magnets;

FIG. 9 is a side view of the device of FIG. 8 shown in its folded position holding tubing of enlarged diameter; and FIG. 10 is a perspective view of an alternate embodiment of the invention in which one bar magnet and a corrugated member having magnetizable elements are shown mounted to the backing strip.

DETAILED DESCRIPTION OF THE PREFERRED EMBODIMENT

Referring to FIG. 1, a tubing holder device 10 is shown. The holder 10 has a backing strip 12 which is generally rectangular in shape except for finger tabs 14 and 16 which protrude outward at each end of the backing strip 12. The purpose of the finger tabs 14,16 will hereinafter be described. The backing strip 12 is a sheet of porous foam plastic material, such as foamed polyurethane. Such material is flexible and light in weight. The backing strip 12 has a first section 15 and a second section 17 which are adapted to be folded at their junction 19 one on top of the other as will hereinafter be described. As shown in the preferred embodiment, mounted on the first section 15 of the backing strip 12 is a first magnet 18. Mounted on the second section 17 is a second magnet 20. A third magnet 22 is mounted on the second section 17 between the first magnet 18 and the second magnet 20.

The magnets 18, 20 and 22 are held in place on the backing strip 12 by an impervious thin plastic laminate 24 which is vacuum formed around each magnet. The laminate 24 is drawn into intimate contact with the backing strip 12 between the magnets by application of suction pressure under the backing strip 12.

The magnets 18, 20, and 22 are spaced to provide preferential receiving locations for tubing. The first preferential receiving location 26 spans the central area of the first magnet 18. The location 26 is preferential since tubing positioned on this location will lie between the second and third magnets 20 and 22 when the strip 12 is in its folded configuration, as will hereinafter be described. A second preferential receiving location 28 forms the area between the first and third magnets 18 and 22. Finally, a third preferential receiving location 30 forms the area between the second and third magnets 20 and 22.

Referring now to FIG. 2, a cross-section of the backing strip 12 and the first magnet 18 is shown. It has been found convenient to use magnets formed of magnetic particles bonded together by an elastomeric material. For example, magnets formed of nitrile rubber embedded with particles of ferromagnetic material, such as barium ferrite, have been found to be highly satisfactory. Magnets of this type may be polarized so that the lower surface which rests on the backing strip 12 constitutes one pole and the upper surface constitutes the other pole. The magnets are cut to form elongated bars or strips. Advantageously, each magnet includes a pair of magnet portions in which upper and lower surfaces have been aligned for opposite polarity. These portions may be separate members or joined integrally. Thus, the first magnet 18 is composed of a magnet portion 32 having a north polarity on its upper surface and a south polarity on its lower surface which is contiguous with a magnet portion 34 having a south polarity on its upper surface and a north polarity on its lower surface. For simplification, only the upper surface polarities are illustrated.

Underlying each magnet is a magnetizable backing member. As shown in FIG. 2, the magnetizable backing member 36 underlies the first magnet 18. The magnetizable backing members block the magnetic field from extending through the back surface of the backing strip 12. This increases the magnetic field of the overlying magnet three to four times.

As shown in FIG. 1, the second and third magnets 20, 22 have magnet portions of upper surface north/south polarity which are oppositely aligned with respect to the upper surface north/south polarity of magnet portions 32, 34 of the first magnet 18. These contiguous magnet portions and the positioning of these portions on each magnet ensures the proper alignment of the first, second, and third magnets 18, 20, and 22 and folded sections of the backing strip 12, when the holder 10 is in its folded configuration, as will hereinafter be described.

Referring now to FIG. 3, the back surface of the backing strip 12 is shown. Affixed to the back surface of the first section 15 of the backing strip 12 is an adhesive 38. The adhesive 38 is covered by a peel-away material 40. Such peel-away material is well known to those of ordinary skill in the art. Similarly, an adhesive (not shown) and a peel-away strip 42 are shown affixed to the back surface of the second section 17 of the backing strip 12, generally below the second and third magnets 20 and 22. In use, one of the peel-away materials 40 or 42 would be removed to expose the adhesive material beneath them. The adhesive material then would be pressed against the substrate to affix that portion of the backing strip 12 to the substrate. The other portion of the backing strip would then remain movable to allow the strip to be folded as will hereinafter be described.

Referring to FIG. 4, the holder 10 is shown affixed to a surgical drape 44, which is commonly made of a paper or cloth material. Specifically, the peel-away material 40 has been removed and the adhesive material 38 affixed to the drape 44. The peel-away material 42 has not been removed so that the second section 17 of the backing strip 12 is movable to permit folding of the device 10. A section of tubing 46 is shown positioned within the second preferential receiving location 28 between the first magnet 18 and the third magnet 22.

Referring to FIG. 5, the holder 10 is shown in its folded configuration. The second section of the backing strip 12 supporting the second and third magnets 20 and 22 is enfolded over the first section 15 of the backing strip 12 supporting the first magnet 18. In this position, the second and third magnets 20 and 22 mutually engage the first magnet 18. The attraction of the first magnet 18 for the second and third magnets 20 and 22 maintains the holder 10 in its folded position and thereby secures the tubing 46 between the folded portions within the second preferential receiving location 28.

FIG. 6 depicts a cross-sectional view of the holder 10 in its folded configuration with the first magnet 18 in mutual engagement with the second magnet 20. The second magnet 20 has a magnet portion 48 of upper surface north polarity and lower surface south polarity and a magnet portion 40 of upper surface south polarity and lower surface north polarity. For simplification and clarity, only the upper surface polarity of each magnet portion 48, 50 is illustrated in FIG. 6. When the holder 10 is folded, the portion 48 of the second magnet 20 is attracted to the portion 34 of the first magnet 18. Similarly, the portion 50 of the second magnet 20 is attracted to the portion 32 of the first magnet 18. As discussed earlier, the upper surface north/south polarities of the portions 32, 34 of the first magnet 18 are oppositely positioned to the upper surface north/south polarities of the portions 48, 50 of the second magnet 20, when the holder 10 is in its unfolded configuration. Thus, when the backing strip 12 is folded, the positioning of the magnet portions ensures that the first and second magnets 18, 20 will have a maximum surface contact. This maximum surface contact not only increases the holding power of the device 10 with respect to the tubing, but also ensures that the backing strip 12, when folded, is properly aligned as shown in FIG. 5. Thus, if the upper surface of the first magnet 18 were of a single polarity and the upper surface of the second magnet 20 were of a single but opposite polarity, when the backing strip 12 would be folded, there would be a possibility that the folded sections would be misaligned, i.e., not directly on top of one another.

When one desires to remove the tubing, one may simply pull upward on the finger tab 16, thereby unfolding the holder device 10 into its coplanar position, as shown in FIG. 4. It is also possible to simply pull upward on the tube section 46 itself, which unfolds the holder 10.

The holding power of the device 10 upon the tubing 46 can be controlled by controlling the magnetic attraction between the second and third magnets 20 and 22, and the first magnet 18. This magnetic attraction is selected to ensure that if one pulls upward on the tubing 46 or the finger tab 16, the holder 10 will unfold rather than tearing the drape 44 or disengaging from the drape 44. Thus, the magnetic hold is less strong than the adhesive hold on the drape.

The quick release of the unfolded position of the holder 10 is also important, when the holder 10 is affixed to the skin of the patient. For example, the holder 10 can be affixed by use of the adhesive 38 to the wrist, forehead, or nose of a patient. The tubing is then positioned within a receiving location, as described above, and held in place by folding the holder 10 and contacting the magnets. In some applications, such as in using a nasal gastric tube, one end of the tubing is inserted into the nostril of the patient. Thus, if the tubing is pulled, such as by sudden movement of the patient's head, the holder 10 will release the tubing, so that the patient's nostril is not harmed. The release of the holder 10 from its folded position ensures safety to the patient in such an application.

Referring to FIG. 7, a side view of the holder in its folded position is shown. In the configuration as shown, the adhesive 38 attached to the back surface of the first section 15 of the backing strip 12 is affixed to the substrate. After positioning a section of tubing 52, within the first preferential receiving location 6, the second section 17 of the backing strip 12 is then folded over the tubing 52.

It should be understood that the tubing 52 may be initially positioned within the third preferential receiving location 30 when the holder is in its unfolded position so that when the first section 15 of the backing strip 12 is folded over the second and third magnets 20, 22, the tubing 52 will be held between folded portions of the backing strip. Thus, in the latter configuration, the adhesive below the peel-away material 42 would be employed to affix the second section 17 to the substrate. This latter configuration is not as preferred as that shown in FIG. 7 if the substrate involved is rigid. This is due to the fact that when the strip is in its folded position, in order for the first magnet 18 to be in surface area contact with the second and third magnets 20, 22, a bulging of the second section 17 at the third preferential receiving location 30 is created. In the latter configuration, a rigid substate would not be able to accommodate this bulge, thereby causing the first magnet 18 to lose significant surface contact with the second and third magnets 20, 22.

The spacing between the second and third magnets 20 and 22 can be designed to be smaller than the spacing between the third magnet 22 and the first magnet 18 to allow smaller diameter tubes to be easily accommodated by positioning them within the first or third preferential receiving locations 26 and 30. Thus, the section of tubing 52 is of smaller diameter than the section of tubing 46.

It should also be understood that the configuration as shown in FIG. 7 is preferable since the tension on the tube 52 can be adjusted by manually spacing the second and third magnets 20, 22 after the strip 12 has been folded. Once the tubing 52 is secured between folded portions of the holder 10, the second and third magnets 20, 22 may be moved closer together so as to more strongly hold the tubing 52.

Referring to FIG. 8, the holder 10 is shown in its unfolded position. In this embodiment, the backing strip 12 supports a first magnet 54 and a second magnet 56 of substantially equal size. This embodiment has a single preferential receiving location 58 spanning the area between the first and second magnets 54, 56. Positioned between the first magnet 54 and second magnet 56 is a peel-away material 57 which covers an adhesive (not shown). The peel-away material 57 is made of a substance which has a substantially lower coefficient of friction than the porous backing strip 12. An example of such a material would be silicone treated-release paper. A tube is then positioned within the preferential receiving location 58 so as to be in contact with the peel-away material 57. When the holder is then folded, the first and second magnets 54, 56 are brought into mutual engagement with the tubing positioned between the folded portions of the holder 10, as shown in FIG. 9.

Referring to FIG. 9, the holder 10 is shown in the folded position with the first magnet 54 and second magnet 56 in mutual engagement. A tubing section 60, which is of larger diameter than the tubing 52, is shown positioned between the folded portions of the backing strip 12. If the peel-away material 57 (not shown) is not removed, this will allow the tubing 60 to be easily slid in an axial direction between the folded portions of the backing strip 12. Conversely, if the peel-away material 57 is removed to expose the adhesive material, then the tubing 60 will be essentially locked in the position, as shown in FIG. 9.

It should be understood that no portion of the surface of the first magnet 54 or second magnet 56 forms a preferential receiving location in this embodiment, since if a tube were to be positioned on either the first or second magnets 54 or 56, and the strip 12 folded, the first and second magnets 54, 56 would not be able to contact each other. The device would not be able to clamp the tubing as required. It should further be understood that the central area of either or both the first and second magnets 54, 56 may be partially cut away to form preferential tube receiving locations. If both the first and second magnets 54, 56 were partially cut away, advantageously, these cut-away areas should be aligned when the holder 10 is in its folded configuration to allow for the clamping of larger diameter tubing and even greater surface contact of the magnets between folded sections of the device.

It should be also understood that any of the magnets can be bent in an arcuate shape to provide a recess and preferential receiving locations for the tubing.

It is also posssible to insert multiple tubes within a single preferential receiving location. For example, at a particular time during an operation, it may be desired to hold both the electrical cord of a cautery and a vacuum tube. Both such tubes would be placed within a preferential receiving location such as the preferential receiving location 57, shown in FIG. 8.

It should also be understood that the holding power of the device is, as depicted in FIG. 1, stronger when the tubing is positioned within the second preferential receiving location 28, as opposed to the first and third preferential receiving locations 26 and 30. Thus, the tubing 46, as shown in FIG. 5, would be more strongly held, given equal magnetic attraction between the magnets than the tubing section 52, as shown in the configuration of FIG. 7. The most important reason for this difference in holding power is that the tube, in its position as shown in FIG. 7, provides greater leverage to pry the magnets apart than does the tube, as positioned in FIG. 5.

Referring to FIG. 10, a further alternate embodiment of the invention is shown in which a first magnet 62 and a corrugated element 64 are mounted on the backing strip 12. The element 64 has recesses 66 which form preferential receiving locations for tubing. Located between the recesses 66 are flat areas 68 which contain magnetizable materials. The areas 68 are flat to maximize surface area contact with the first magnet 62 when the strip 12 is folded. The composition of the element 64, other than the magnetizable areas 68, may be made of porous foam or may be completely magnetizable. Thus, in the latter embodiment, the element 64 may be a metal strip. The recesses 66 may be of different sizes and contours to accommodate tubing of different shapes and dimensions.

The embodiment of FIG. 10 illustrates that it is not necessary that multiple magnets be mounted on the backing strip 12. Rather, it is only necessary that one of the members be a magnet and the other be a magnetic material, i.e., one which can be magnetized, such as a member made from iron, cobalt, or nickel. Such magnetizable members are well known in the art.

It should also be understood that the backing strip 12 may be increased in thickness with tube receiving recesses cut into the strip itself. Mutually attracting magnetic materials may be mounted on each folding portion of the strip to maintain the strip in its folded configuration, thereby securing tubing within the recesses.

Finally, it should be understood that the holder 10 may also be used to hold a device such as a clamp or ring stand which are intended to be included within the definition of "tubing". Moreover, "tubing" also includes elongated members which have non-circular, such as square, configurations.

What is claimed is:

1. A medical tube holder comprising:
   (a) a backing strip having front and back surfaces, said strip having first and second sections adapted to be folded at their junction one on top of the other;
   (b) a first magnetic material mounted on the front surface of said first section;
   (c) a second magnetic material spaced from said first magnetic material and mounted on the front surface of said second section;
   (d) a third magnetic material spaced from said first and second magnetic materials and mounted on the front surface of said second section between said first and second magnetic materials, said first magnetic material having magnetic attraction for said second and third magnetic materials;
   said first, second and third magnetic materials being positioned so that said second and third magnetic materials mutually engage said first magnetic material when said strip is folded along said junction, the space between said first and third magnetic materials forming a first preferential tube receiving location, the space between said second and third magnetic materials forming a second preferential tube receiving location, said strip being adapted to secure tubing within said locations between said sections when in their folded position.

2. The holder of claim 1 wherein said third magnetic material is spaced further from said first magnetic material than said second magnetic material so that said first preferential tube receiving location is larger than said second tube receiving location to accommodate tubing of larger diameter.

3. A method of holding medical tubing comprising:
(a) providing a backing strip having front and back surfaces, having first, second and third members spaceably mounted on said front surface, said third member mounted between said first and second members, said first member having a mutual magnetic attraction with said second and third members, and having a preferential tube receiving location between said second and third members;
(b) placing a tube within said preferential tube receiving location;
(c) folding said strip to permit said first member to contact said second and third members and secure said tube within said preferential tube receiving location between folded portions of said strip.

* * * * *